US009775782B2

(12) United States Patent
Delegge et al.

(10) Patent No.: US 9,775,782 B2
(45) Date of Patent: Oct. 3, 2017

(54) ELONGATED DILATOR FOR PULL PEG TUBE WITHOUT A LOOP (71) Applicant: Cook Medical Technologies LLC, Bloomington, IN (US)

(72) Inventors: Rebecca C. Delegge, Mt. Pleasant, SC (US); Mark H. Delegge, Mt. Pleasant, SC (US)

(73) Assignee: Cook Medical Technologies LLC, Bloomington, IN (US)

( * ) Notice: Subject to any disclaimer, the term of this patent is extended or adjusted under 35 U.S.C. 154(b) by 86 days.

(21) Appl. No.: 14/774,425

(22) PCT Filed: Feb. 12, 2014

(86) PCT No.: PCT/US2014/016005
§ 371 (c)(1),
(2) Date: Sep. 10, 2015

(87) PCT Pub. No.: WO2014/158399
PCT Pub. Date: Oct. 2, 2014

(65) Prior Publication Data
US 2016/0038379 A1 Feb. 11, 2016

Related U.S. Application Data (60) Provisional application No. 61/783,950, filed on Mar. 14, 2013.

(51) Int. Cl.
*A61J 15/00* (2006.01)
*A61M 29/00* (2006.01)
(Continued)

(52) U.S. Cl.
CPC ....... *A61J 15/0019* (2013.01); *A61B 17/3415* (2013.01); *A61J 15/0015* (2013.01);
(Continued)

(58) Field of Classification Search
CPC ................ A61J 15/0017; A61J 15/0023; A61J 15/0015; A61J 15/0069; A61M 2025/0191; A61B 17/3415
See application file for complete search history.

(56) References Cited

U.S. PATENT DOCUMENTS 5,167,627 A * 12/1992 Clegg ................ A61B 17/3415
604/103.03
5,409,004 A * 4/1995 Sloan ..................... A61B 6/502
600/434
(Continued)

FOREIGN PATENT DOCUMENTS

WO  WO 2005/074819 A2   8/2005
WO  WO 2007/027920 A1   3/2007

OTHER PUBLICATIONS

International Search Report and Written Opinion for priority application PCT/US2014/016005, dated May 19, 2014.

*Primary Examiner* — Nathan R Price
*Assistant Examiner* — John Doubrava
(74) *Attorney, Agent, or Firm* — Brinks Gilson & Lione (57) ABSTRACT A feeding tube and method for introducing a feeding tube within the gastrointestinal tract of a patient, whereby the feeding tube is introduced by using a variation of the Ponsky "pull" method of feeding tube placement. The feeding tube comprises an elongate shaft having a distal end and proximal end. The feeding tube also comprises a coupling structure for coupling the feeding tube to a pull wire, the coupling structure being internal to and proximal of the distal end of the feeding tube shaft. The coupling structure is configured to engage an outwardly biased anchor member affixed to the end of the pull wire. The feeding tube is introduced within the patient by attaching the anchor member of the previously placed pull wire to the coupling structure of the feeding tube, and then pulling the pull wire so as to pull the feeding tube into and through the gastrointestinal tract of the patient.

18 Claims, 5 Drawing Sheets (51) Int. Cl.
    *A61B 17/34*     (2006.01)
    *A61M 25/02*     (2006.01)
    *A61M 25/09*     (2006.01)

(52) U.S. Cl.
    CPC ....... *A61J 15/0034* (2013.01); *A61J 15/0061* (2013.01); *A61M 29/00* (2013.01); *A61J 15/0042* (2013.01); *A61M 2025/0233* (2013.01); *A61M 2025/09125* (2013.01)

(56) References Cited

U.S. PATENT DOCUMENTS

| | | |
|---|---|---|
| 6,527,748 B1 | 3/2003 | Suzuki |
| 7,018,373 B2 * | 3/2006 | Suzuki ............... A61B 17/3415 600/114 |
| 2002/0002361 A1 | 1/2002 | Fanelli et al. |
| 2002/0010437 A1 | 1/2002 | Lopez et al. |
| 2003/0229334 A1 | 12/2003 | Suzuki |
| 2005/0020875 A1 * | 1/2005 | Delegge ............. A61J 15/0019 600/101 |
| 2007/0078397 A1 | 4/2007 | Weststrate |
| 2007/0106217 A1 * | 5/2007 | DeLegge ........... A61B 17/3415 604/104 |
| 2008/0039797 A1 | 2/2008 | Abe et al. |
| 2012/0016298 A1 | 1/2012 | DeLegge et al. |

\* cited by examiner

ELONGATED DILATOR FOR PULL PEG TUBE WITHOUT A LOOP

CROSS-REFERENCE TO RELATED APPLICATIONS

This application is a 371 national stage application of PCT Application No. PCT/US2014/016005, filed Feb. 12, 2014, which application claims the benefit of U.S. Provisional Application No. 61/783,950, filed Mar. 14, 2013, both of which are titled "Elongated Dilator For Pull Peg Tube Without A Loop", the contents of which are incorporated herein by reference.

TECHNICAL FIELD

The present invention relates to medical devices, and more particularly to feeding tubes for delivery of nutritional products to the intestinal tract and methods for placement of feeding tubes therein.

BACKGROUND OF THE INVENTION

Patients for which normal ingestion of food becomes difficult or impossible may require placement of a feeding tube to assist in providing their nutritional needs. For some individuals, such as comatose patients, stroke victims, or those with a compromised gastrointestinal tract, this may require placement of a tube that is introduced percutaneously into the stomach for delivery of nutritional products directly into the stomach or jejunum. The procedure, known as a Percutaneous Endoscopic Gastrostomy (PEG), involves the introduction of an endoscope into the stomach, while the desired site where the stoma is to be created is indicated from above by depressing the abdomen. Transillumination may also be utilized to locate the desired site through the abdominal wall. A sheathed needle or trocar punctures the abdominal wall and enters the stomach, creating a stoma. The needle is removed and a looped insertion or pull wire is introduced through the sheath where it is grasped by a snare or forceps deployed from the working channel of the endoscope. Once it is captured, the insertion wire is pulled into the working channel of the endoscope. The endoscope is then withdrawn from the patient via the oral cavity, pulling the insertion wire with it.

In the standard Ponsky method (or "pull" method), the percutaneous gastrostomy feeding tube is coupled to the portion of the insertion wire exiting the patient's mouth. More specifically, the loop of the insertion wire is knotted or tied to a loop attached to the distal end of the gastrostomy feeding tube. With the insertion wire now tethered to the gastrostomy feeding tube, the endoscopist retracts the portion of the insertion wire exiting the stoma, thereby pulling the gastrostomy feeding tube into the patient's mouth and towards the stomach. With continued retraction of the insertion wire, the distal end of the gastrostomy feeding tube is pulled out through the stoma. The gastrostomy feeding tube typically includes a tapered dilator portion to aid its passage through the stoma. Once the feeding tube has been properly positioned with the proximal end cap or bolster of the feeding tube against the internal wall of the stomach, it is secured by an external bolster positioned against the outside of the abdomen wall. The endoscope is typically reintroduced into the stomach to check the internal position of the feeding tube before the external bolster is secured. The dilator portion of the feeding tube, including the insertion wire tied thereto, is then cut away and removed and an adapter compatible with standardized feeding pumps and syringes is attached.

Conventional gastrostomy feeding tubes specifically configured for placement by the standard "pull" method have a number of drawbacks. For example, conventional "pull" type gastrostomy feeding tubes typically have a loop of wire affixed to the distal end of the dilator for attachment to the insertion wire. This attachment loop may be subjected to significant pulling forces as the gastrostomy feeding tube is pulled, via the insertion wire, through the mouth, esophagus and stomach of the patient. The manner of securing the attachment loop to the dilator must therefore be substantial, which may necessitate a larger dilator than would otherwise be desired. In addition, the attachment loop may become detached from the dilator during the "pull" method of insertion, thereby necessitating that the feeding tube be removed and the placement procedure be re-started with a new feeding tube. There is also the possibility that the insertion wire may separate from the feeding tube attachment loop during the placement procedure. For example, the knot that is used to secure the loop of the insertion wire to the attachment loop may become untied, thereby necessitating that the procedure be started over by re-advancing the end of the insertion wire out of the patient's mouth and re-tying it to the feeding tube. Moreover, the step of securely tying the insertion wire to the feeding tube attachment loop may be time consuming and difficult. Finally, the knot between the insertion wire and the feeding tube tends to snag on or irritate the tissue of the esophagus, stomach, and stoma as it is being pulled therethrough.

What is needed is a gastrostomy feeding tube that can be introduced using the "pull" method, and which can be quickly and securely attached to an insertion or pull wire, which can be secured to the pull wire without tying or knotting the pull wire to the feeding tube, and which does not include or rely on a loop of wire affixed to the dilator portion of the feeding tube.

SUMMARY OF THE INVENTION

The foregoing problems are solved and a technical advance is achieved with an illustrative feeding tube and method for introducing a feeding tube within the gastrointestinal tract of a patient, whereby the feeding tube is introduced using a variation of the Ponsky "pull" method of feeding tube placement. The feeding tube comprises an elongate shaft having a distal end and proximal end. The feeding tube also comprises a coupling structure for coupling the feeding tube to a pull wire, the coupling structure being internal to and proximal of the distal end of the feeding tube shaft. The feeding tube is introduced within the patient by attaching the previously placed pull wire to the coupling and guiding structures of the feeding tube, and then pulling the pull wire so as to pull the feeding tube into and through the gastrointestinal tract of the patient. The coupling structure eliminates the need for a separate attachment loop affixed to the distal end of the feeding tube. The coupling structure also eliminates the difficulties and problems associated with tying the pull wire to an attachment loop on the feeding tube.

In one aspect of the invention, the coupling structure comprises a portion of the feeding tube, such as the dilator, within which the elongate pull member is secured. In other aspects of the invention, the coupling structure comprises an internal shoulder or catch for engaging an anchor member attached to the end of the pull wire. In still other aspects of the invention, the anchor member comprises an anchor bar that is affixed to the end of the pull wire and is biased so as to extend along a transverse or acute angle relative to the pull wire, wherein an end of the anchor bar is configured to engage the catch of the dilator coupling structure. The anchor bar is movable to a collapsed configuration having a reduced profile to enable coupling to the dilator. Once engaged, the coupling structure prevents the pull wire from disengaging from the feeding tube.

The feeding tube is introduced within the patient by securing the anchor member to the coupling structure of the feeding tube. More specifically, the feeding tube is secured to the portion of the pull wire extending out of the patient's mouth. The portion of the pull wire extending out through the stoma of the patient, which is opposite of the looped portion, is then pulled so as to pull the feeding tube through the mouth of the patient and into the gastrointestinal tract using a variation of the Ponsky "pull" method of placement. Other aspects of the procedure for the final positioning and placement of the feeding tube according to the present invention are similar to the procedure used for final positioning and placement of a standard feeding tube.

These and other advantages, as well as the invention itself, will become apparent in the details of construction and operation as more fully described below. Moreover, it should be appreciated that several aspects of the invention can be used with other types of stent delivery catheters or medical devices.

DESCRIPTION OF THE INVENTION

Various embodiments of the feeding tube 10 according to the present invention are shown in FIGS. 1-9. In general, the feeding tube 10 comprises an elongate tubular shaft 12 having a proximal end 14 and a distal end 16. A feeding lumen 18 extends through at least a portion of the shaft 12 and provides a passageway for the delivery of nutritional products or medications directly into the gastrointestinal tract of the patient. An exemplary embodiment of a feeding tube according to the present invention is a percutaneous endoscopic gastrostomy (or PEG) feeding tube 20 (shown in FIG. 1) that is positioned through the stomach and abdominal walls of the patient. The PEG feeding tube 20 allows the delivery of nutritional products or medications directly into the patient's stomach. As will be explained in greater detail below, the PEG feeding tube 20 is introduced into and placed within the patient by coupling the feeding tube 20 to a pull wire 22 that has been previously placed through the gastrointestinal tract of a patient, and then pulling the pull wire 22 so as to pull the feeding tube 20 into the patient's stomach using a variation of the Ponsky "pull" method of feeding tube placement.

In general, the feeding tube 10 comprises a coupling structure 26 for receiving and securing the elongate pull wire 22 to the feeding tube. In particular, the coupling structure 26 is configured to engage an anchor bar 24 affixed to the end of the pull wire 22. In embodiment illustrated in FIGS. 1-4, the coupling structure 26 comprises a catch 28 that is disposed along the distal portion of the elongate shaft 12 at a location that is proximal to the distal end 16. The catch 28 comprises a shoulder or widened area 60 along the interior surface 62 of the lumen 48 that engages an end 64 of the anchor bar 24. As will be explained in greater detail below, the anchor bar 24 and catch 28 eliminate the need for a separate loop affixed to the distal end of the feeding tube for attachment to the pull wire, and also eliminate the difficulties and problems associated with tying the pull wire to an attachment loop on the feeding tube. The lumen 48 of the dilator or feeding tube 10 is preferably configured to direct the pull wire 22 toward the distal end 16 of the feeding tube 10 so as to maintain the pull wire 22 in substantial alignment with the distal end of the feeding tube 10 during the placement procedure.

Figure 1:
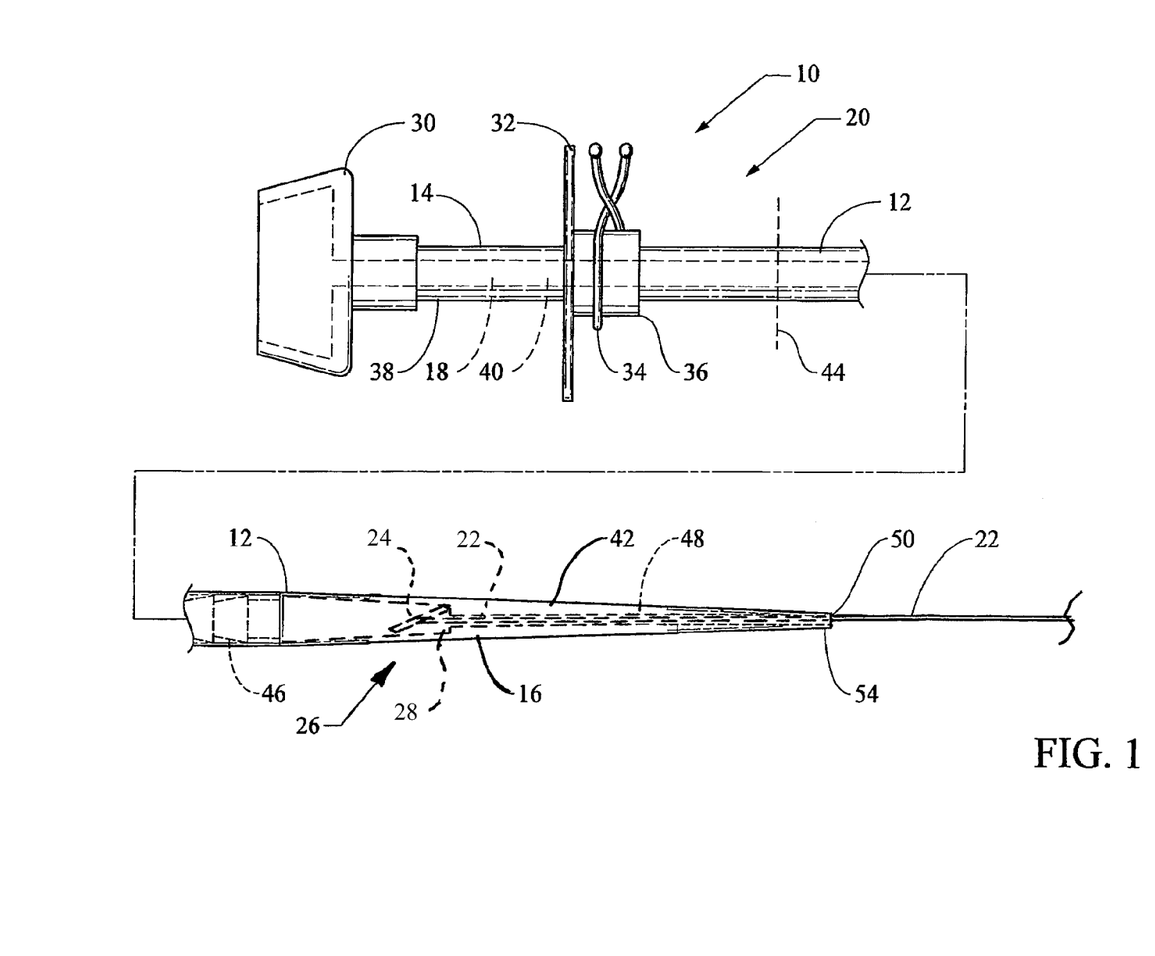
FIG. 1 is a side view of one embodiment of the feeding tube of the present invention, and in particular a short wire gastrostomy (or PEG) feeding tube.

In the embodiment illustrated in FIG. 1, the feeding tube 10 comprises a pull type percutaneous endoscopic gastrostomy (or PEG) feeding tube 20 that can be introduced within the patient with a pull wire 22 using a variation of the Ponsky "pull" method of introduction. The PEG feeding tube 20 comprises an elongate shaft 12 having a distal end 16 and a proximal end 14. An internal bolster (or bumper) 30 is affixed to the proximal end 14 of the shaft 12 and is configured to engage the interior surface of the stomach wall. In the particular embodiment illustrated, the overall length of the shaft 12 is between 105 and 145 cm. An exterior bolster 32 is provided and is configured to attach to the shaft 12 so as to engage the exterior surface of the abdomen. In the embodiment illustrated, the external bolster 32 is secured to the shaft 12 by a spring clamp 34 that presses the sleeve 36 of the external bolster 32 into frictional engagement with the exterior surface of the shaft 12. However, other types and designs of internal and external bolsters 30, 32 may be employed. For example, internal bolster 30 may comprise an inflatable balloon or other expandable structure.

The proximal portion of the shaft 12 comprises a feeding catheter 38 having a feeding lumen 40 disposed therethrough. In the particular embodiment illustrated, the feeding catheter 38 comprises an 18-24 French tube having a 4-5.5 mm diameter feeding lumen 40. The distal portion of the shaft 12 comprises a removable lead catheter 42, commonly referred to as a dilator, which is preferably tapered to facilitate ingress through the gastrointestinal tract of the patient. The dilator 42 and the feeding catheter 38 may be manufactured as separate components and joined together via an attachment structure, such as barbed connector 46, or may be manufactured as a unitary structure. As will be explained in greater detail below, the dilator 42 is removed from the feeding catheter 38 by, for example, severing the shaft 12 along cut line 44.

Figure 2:
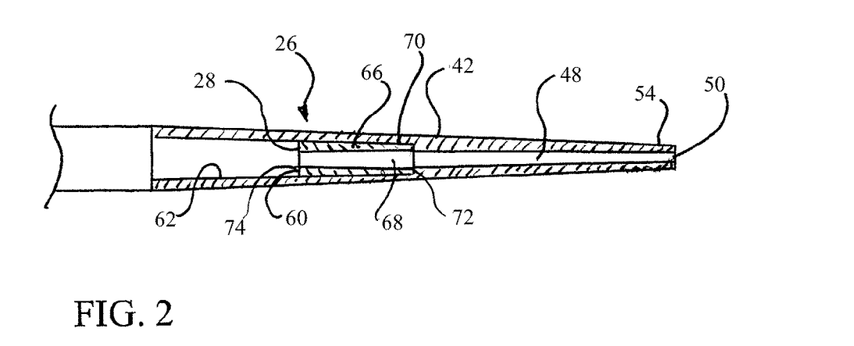
FIG. 2 is a cross-sectional side view of the dilator portion of the feeding tube of FIG. 1 without a pull wire coupled thereto.
Figure 3:
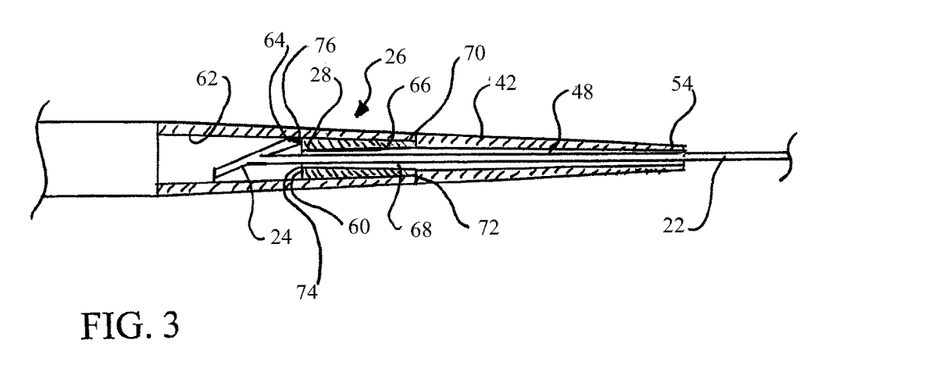
FIG. 3 is a cross-sectional side view of the dilator portion of the feeding tube of FIG. 1 coupled to an exemplary pull wire.

In the embodiment illustrated in FIGS. 1-3, the lumen 48 extends through a portion of the elongate shaft 12, and in particular, through a portion of the dilator 42. The lumen 48 is sized to permit the pull wire 22 and anchor bar 24 to pass there through and extends proximally from a distal opening or port 50 near the distal end 16 of the shaft 12. The lumen 48 extends a sufficient distance proximally of the catch 28 to accommodate anchor bar 24 (see FIG. 3). The lumen 48 may extend through the entire length of the dilator 42 and be in communication with feeding lumen 18 of shaft 12. In the particular embodiment illustrated, the distal opening 50 is disposed in the distal tip 54 of the dilator 42, and the catch 28 is spaced approximately 5-10 cm from the distal opening 50.

The anchor bar 24 and catch 28 eliminate the need for a separate loop affixed to the distal end of the feeding tube 10 for attachment to the pull wire 22, and also eliminate the difficulties and problems associated with tying the pull wire 22 to an attachment loop on the feeding tube. More specifically, the catch 28 provides an efficient method for securing the anchor bar 24 of the pull wire 22 to the dilator 42 without the need to tie the pull wire 22 to any portion of the feeding tube 10. The catch 28 also provides for an attachment location that is on the interior of the dilator 42, thereby reducing external components or surface features that could cause resistance or tissue damage during placement. The catch 28 further provides for an attachment location that is spaced proximally from the distal tip 54 of the dilator 42, thereby allowing for a reduction in size of the distal tip 54. Moving the spacing the attachment location proximally from the distal tip 54 also reduces the likelihood that the feeding tube 10 will inadvertently separate from the pull wire 22 during the placement procedure.

The lumen 48 of the dilator 42 guides the pull wire 22 from the coupling structure 26 to the distal tip 54 of the dilator 42. As a result, the lumen 48 directs the pulling force (applied by the pull wire 22 to the dilator 42) through the distal tip 54, which helps to guide the distal tip 54 along a central pathway as the feeding tube is being pulled through the patient's gastrointestinal tract. Guiding the distal tip 54 along a central pathway reduces the chance of snagging and irritation to the tissue of the bodily lumen that may be caused by the distal tip 54 during its introduction. This also reduces the frictional forces that are encountered by the feeding tube 10 during its introduction and placement, thereby reducing the amount of pulling force required to pull the feeding into and through the patient.

As best seen in FIG. 2, the coupling structure 26 comprises a tubular metal insert 66 with a lumen 68 extending longitudinally there through. The distal end 72 of the lumen 68 has a diameter that matches the diameter of the proximal end of the dilator lumen 48 so that the juncture between the lumens 48, 68 does not comprise a step or ridge that would interfere with the passage of the pull wire 22 there through. In other words, the interior surface of the insert lumen 68 at the distal end 72 is flush with the dilator lumen 48. This configuration is accomplished by providing a recess 70 in the interior surface 62 of the dilator lumen 48 to accommodate the insert 66 therein. The proximal end 74 of the insert lumen 68 has a diameter that is less than the diameter of the dilator lumen 48 so as to form a widened area or should 60. As best seen in FIG. 3, it is this shoulder 60 against which the end 64 of the anchor bar 24 engages to secure the pull wire 22 to the feeding tube 10.

In the particular embodiment illustrated, the shoulder 60 is perpendicular to the longitudinal axis of the dilator 42. However, the shoulder 60 may be disposed at an angle such that the exterior circumference of the shoulder 60 is disposed distally of the interior circumference such that the surface tends to push or bias the end 64 of the anchor bar 24 outwardly.

In the particular embodiment illustrated in FIG. 3, the insert lumen 68 is tapered along the length thereof such that the proximal end 74 of the lumen 68 has a smaller diameter than the distal end 72 of the lumen 48. The taper increases the width of the shoulder 60 and thereby reduces the possibility that the end 64 of the anchor bar 24 will disengage or slip therefrom. The taper also helps to collapse or compress the anchor bar 24 against (i.e., longitudinally align with) the side of the pull wire 22 as it passes through the insert lumen 68 during coupling. However, it should be understood that the insert lumen 48 may comprises a uniform diameter along the length thereof.

In the preferred embodiment, the insert 66 comprises a metal material such as stainless steel. Although other materials may be utilized, the insert 66 must be of sufficient strength and rigidity to transfer the pulling forces applied by pull wire 22 to the feeding tube 10 without rupturing or deforming the dilator 42.

Figure 4:
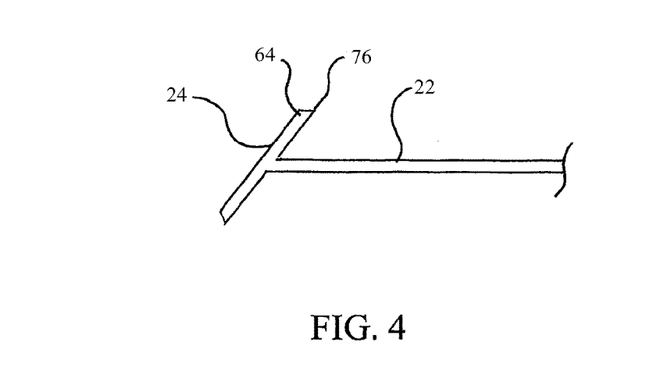
FIG. 4 is a perspective view of the exemplary pull wire.

An exemplary embodiment of the pull wire 22 and anchor bar 24 is illustrated in FIG. 4. The connection between the anchor bar 24 and the end of the pull wire 22 must be of sufficient strength to transfer the pulling forces from the pull wire 22 to the feeding tube 10. In addition, the connection between the anchor bar 24 and the pull wire 22 should be configured to bias the anchor bar 24 at an acute or transverse angle relative to the longitudinal axis of the pull wire 22. More specifically, the connection between these components should be such that distally directed force on the pull wire 22 tends to move or rotate the anchor bar 24 along an acute angle relative to the pull wire 22, for example, in the configuration illustrated in FIG. 4. This causes the end 64 of the anchor bar 24 to move away from the pull wire 22 a sufficient distance to engage the shoulder 60 of the catch 28 of the coupling structure 26, as illustrated in FIG. 3.

In the particular embodiment illustrated, the end of the pull wire 22 has a flexibility that is greater than that of the anchor bar 24. This allows the end of the pull wire 22 to bend or curve as it passes through dilator lumen 48 and insert lumen 68. Bending of the end of the pull wire 22 is necessary to allow the anchor bar 24 to be collapsed or compressed against the side of the pull wire 22 as the anchor bar 24 is pushed through the lumens 48, 68. Alternatively, the connection between the pull wire 22 and the anchor bar 24 may be sufficiently flexible to allow the end 64 of the anchor bar 24 to be collapsed against the side of the pull wire 22 during the step of coupling. For example, a hinged connection could be utilized. However, and as explained above, the connection should be configured to bias the anchor bar 24 at an acute or transverse angle relative to the longitudinal axis of the pull wire 22 once the anchor bar 24 is pushed proximally of the catch 28 of the coupling structure.

Figure 5:
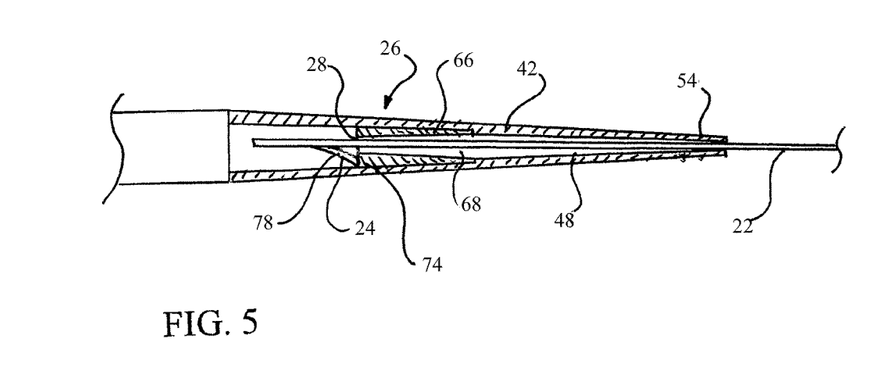
FIG. 5 is a cross-sectional side view of a dilator portion of the feeding tube coupled to another embodiment of a pull wire.

In the embodiment illustrated in FIG. 4, the end 64 of the anchor bar 24 is angled to provide a tapered surface. The tapered surface creates an engagement point 76 that, as shown in FIG. 5, is configured to engage the shoulder 60 of the catch 28 at a location that is spaced inwardly from the interior surface 62 of the dilator 42, and preferably at a mid-point of the shoulder 60. This prevents the end 64 of the anchor bar 24 from pushing into and between the outside surface of the insert 66 and the interior surface 62 of the dilator 42. The engagement point 76 is also preferably configured to slightly penetrate the surface of the shoulder 60, which reduces the likelihood that the anchor bar 24 will disengage from the catch 28 during the feeding tube 10 placement procedure.

FIG. 5 illustrates an alternative embodiment of the pull wire 22 and anchor bar 24. The anchor bar 24 comprises a single flexible barb 78 that projects outwardly and distally from the side of the pull wire 22. The barb 78 is sufficiently flexible to permit the barb 78 to be collapsed against the side of the pull wire 22 to permit these components to pass through the lumens 48, 68 during the coupling procedure. Nevertheless, the barb 78 should be biased or configured to assume the position shown in FIG. 5 once the barb 78 passes proximally of the proximal end 74 of the insert 66 (i.e., catch 28). In the particular embodiment illustrated, the anchor bar 24 comprises a single barb 78, although a plurality of barbs 78 may be utilized.

Figure 6:
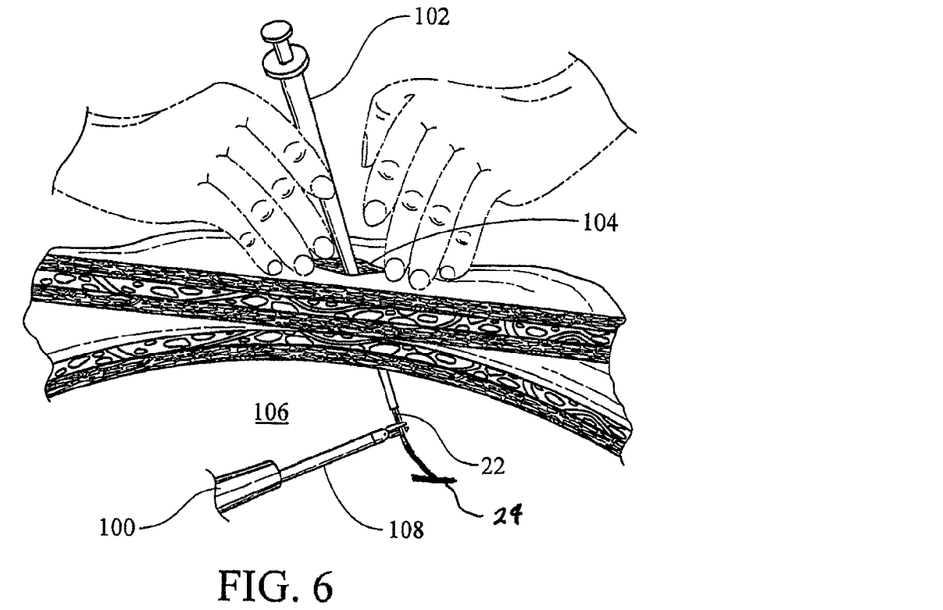
FIGS. 6-9 illustrate successive steps in an exemplary method of introducing and placing the embodiment of the feeding tube of FIG. 1 into the gastric lumen of a patient.

The PEG feeding tube 20 of FIG. 1 is introduced within the patient using a variation of the standard Ponsky "pull" method of placement. An exemplary embodiment of this procedure is illustrated in FIGS. 6-9. With reference to FIG. 6, an endoscope 100 is introduced through the mouth and into the stomach of the patient. A standard Esophagogastroduodenoscopy (EGD) is then typically performed with the endoscope. An EGD is an examination of the lining of the esophagus, stomach, and upper duodenum with the endoscope's camera. The endoscope is then used to identify the desired site where the stoma is to be created. The site is typically identified by depressing the abdomen from outside the patient. Transillumination may also be utilized to locate the desired site through the abdominal wall. For example, the room lights are dimmed so that the light emitted from the end of the endoscope can be seen from outside the patient (i.e., through the stomach and abdominal wall tissue). Once the target site has been identified, a trocar or sheathed needle 102 punctures the abdominal and stomach walls to create a stoma 104, with the distal end of needle 102 entering the interior of the stomach cavity 106. The needle 102 is removed and a pull wire 22 is introduced through the sheath and into the stomach cavity 106. The anchor bar 24 or distal end of the pull wire 22 is then grasped by grasping device 108, such as a snare or forceps, which is deployed from the working channel of the endoscope 100. Once end of the pull wire 22 is captured, the grasping device 108 is retracted so as to pull distal end of the pull wire 22 into the working channel of the endoscope 100. The anchor bar 24 may be temporarily bonded to the side of the pull wire 22 to facilitate pulling the anchor bar 24 into the endoscope. The endoscope 100 is then withdrawn from the patient via the oral cavity, pulling the distal end of the pull wire 22 with it.

Figure 7:
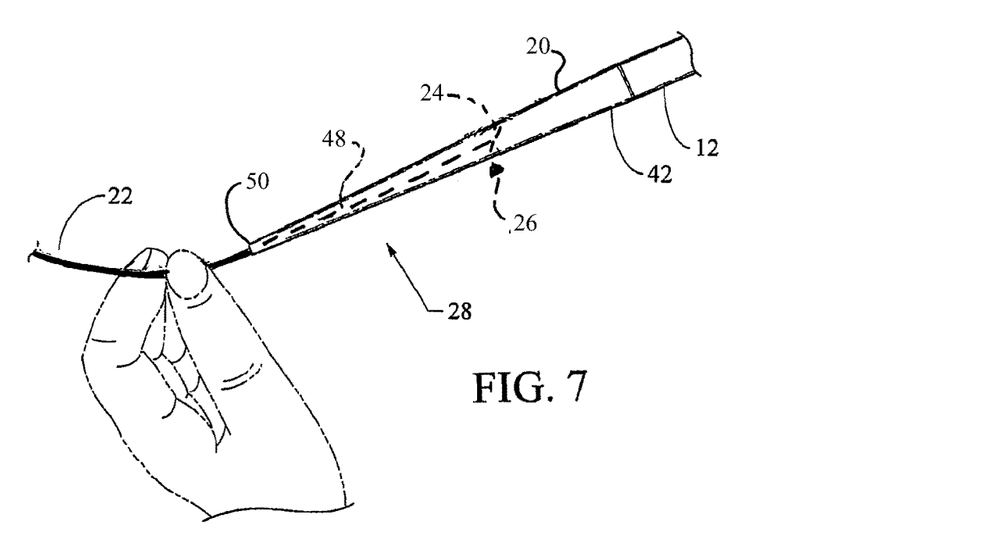

With reference to FIG. 7, the PEG feeding tube 20 is introduced within the patient by first coupling the distal end of the feeding tube shaft 12 to the distal end of the pull wire 22. In particular, the portion of the pull wire 22 extending out from the patient's mouth (i.e., anchor bar 24) is inserted in through the distal opening 50, along the lumen 48, and into engagement with coupling mechanism 26. In particular, the anchor bar 24 is pushed past catch 28, where upon it is allowed to rotate into engagement with the interior wall of the lumen 48 (see FIG. 3). The pull wire 22 is then pulled distally until the anchor bar 24 engages catch 28.

Figure 8:
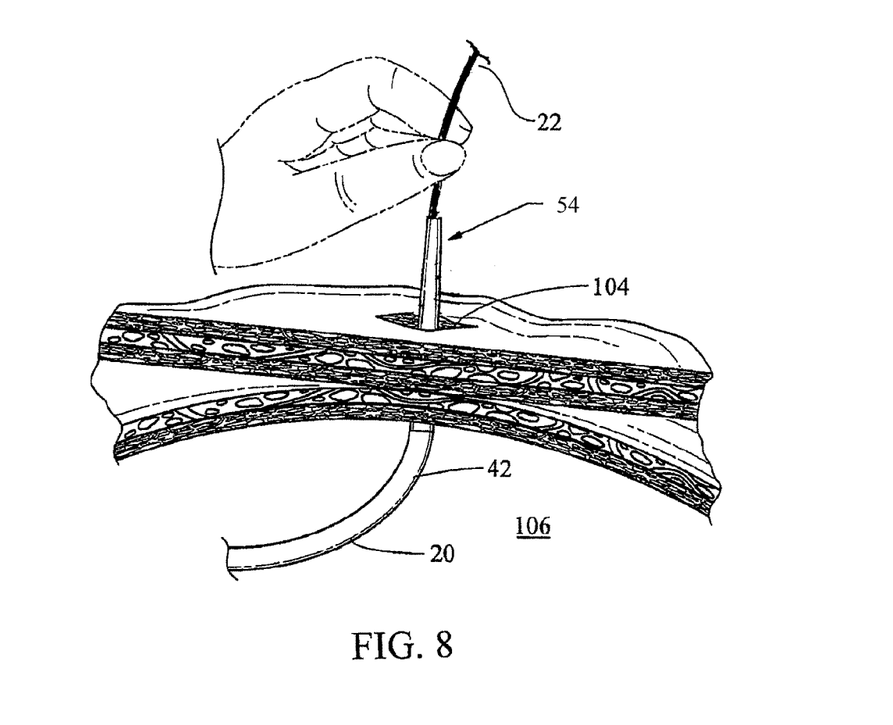

With reference to FIG. 8, the proximal end of the pull wire 22, i.e., the portion extending out of the stoma 104, is then grasped and pulled away from the patient. This pulling action pulls the dilator 42 of the PEG feeding tube 20 to be pulled through the mouth and into the gastrointestinal tract of the patient. With continued pulling of the pull wire 22, the dilator 42 of the feeding tube 20 is pulled into the patient's stomach 106. As illustrated in FIG. 8, further retraction of the pull wire 22 causes the distal end 16 of the shaft 12 (i.e., dilator 42) to be pulled out through the stoma 104. As noted above, the dilator 42 of the feeding tube 20 preferably includes a tapered dilator portion (see FIG. 1) to aid its passage through the stoma 104. Once the dilator 42 passes out through the stoma 104, the pull wire 22 may be removed (disengaged) from the feeding tube 20. The endoscope 100 may then be reintroduced into the stomach cavity 106 to check the position of the feeding tube 20 (i.e., the position of the internal bolster 30).

Figure 9:
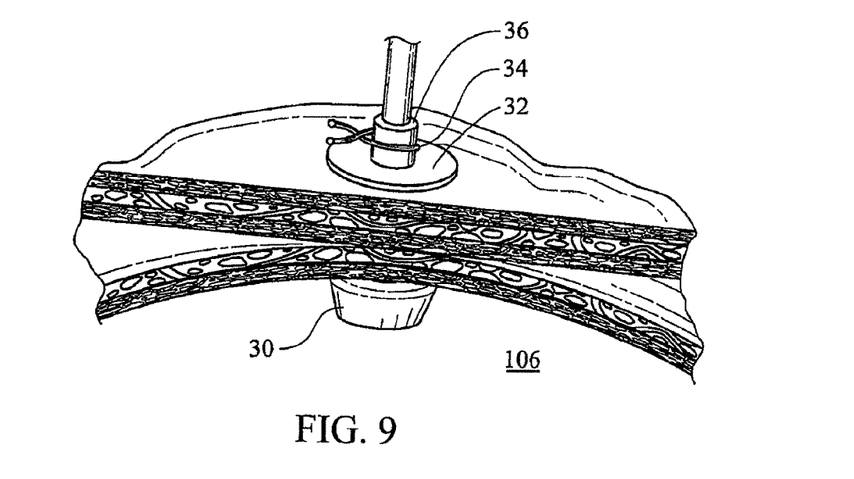

As illustrated in FIG. 9, once the feeding tube 20 has been properly positioned with the internal bolster 30 of the feeding tube against the internal wall of the stomach, it is secured by an external bolster 32 secured to the shaft 12 and positioned against the outside of the abdomen wall. The dilator 42 is then cut away and removed and an adapter compatible with standardized feeding pumps and syringes is attached. Other aspects of the procedure for the introduction and placement of the PEG feeding tube 20 not described herein are similar to the standard Ponsky "pull" procedure for introduction and placement of a standard PEG tubes and have not been repeated here.

While there have been described what are presently believed to be the preferred embodiments of the invention, those skilled in the art will realize that changes and modifications may be made thereto without departing from the spirit of the invention. It is to be understood that the invention can be carried out by specifically different equipment and devices, and that various modifications, both as to the equipment details and operating procedures, can be accomplished without departing from the scope of the invention itself.

The invention claimed is:

1. A system for placement of a feeding tube apparatus into the stomach of a patient using an elongate pull wire having an anchor structure attached to an end thereof, the system comprising:
   an elongate pull wire having an anchor structure fixedly connected to an end thereof, the anchor structure comprising an engagement end movable between a collapsed position adjacent to the pull wire and an expanded position spaced apart from the pull wire; and
   a feeding tube apparatus comprising:
      an elongate tubular portion having a feeding lumen extending through at least a portion thereof and configured to traverse a stoma through the patient's stomach and abdominal walls;
      a bolster fixedly connected to a proximal end of the tubular portion, the bolster having an enlarged cross-section configured to prevent egress thereof through the stoma; and
      a tapered dilator connected to a distal end of the tubular portion and having a distal tip at the distal end thereof, the dilator comprising a dilator lumen extending proximally from the distal tip, the dilator further comprising a coupling structure disposed within the dilator lumen and proximal of the distal tip, the coupling structure including a catch circumferentially disposed about an interior surface of the dilator lumen, the catch being configured to engage the engagement end of the anchor structure when in the expanded position,
      wherein the catch extends completely about the interior surface of the dilator and comprises a uniform profile that is configured to engage the engagement end of the anchor bar irrespective of a rotational orientation of the anchor bar relative thereto.

2. The system according to claim 1 wherein the anchor structure comprises an anchor bar biased at an angle relative to a longitudinal axis of the pull wire, the engagement end being disposed on an end of the anchor bar.

3. The system according to claim 2 wherein the end of the anchor bar comprises an end surface that is disposed at an acute angle relative to an axis of the anchor bar.

4. The system according to claim 1 wherein the anchor structure comprises an outwardly projecting flexible barb, the engagement end being disposed on an end of the barb.

5. The system according to claim 1 wherein the catch is disposed at a perpendicular angle to a longitudinal axis of the dilator.

6. A system for placement of a feeding tube apparatus into the stomach of a patient using an elongate pull wire having an anchor structure attached to an end thereof, the system comprising:
   an elongate pull wire having an anchor structure fixedly connected to an end thereof, the anchor structure comprising an engagement end movable between a collapsed position adjacent to the pull wire and an expanded position spaced apart from the pull wire; and
   a feeding tube apparatus comprising:
      an elongate tubular portion having a feeding lumen extending through at least a portion thereof and configured to traverse a stoma through the patient's stomach and abdominal walls;
      a bolster fixedly connected to a proximal end of the tubular portion, the bolster having an enlarged cross-section configured to prevent egress thereof through the stoma; and
      a tapered dilator connected to a distal end of the tubular portion and having a distal tip at the distal end thereof, the dilator comprising a dilator lumen extending proximally from the distal tip, the dilator further comprising a coupling structure disposed within the dilator lumen and proximal of the distal tip, the coupling structure including a catch circumferentially disposed about an interior surface of the dilator lumen, the catch being configured to engage the engagement end of the anchor structure when in the expanded position,
   wherein the catch extends inwardly from the interior surface of the dilator lumen, and wherein the anchor structure comprises an anchor bar affixed to the end of the pull wire, the anchor bar being biased at an angle relative to a longitudinal axis of the pull wire, the engagement end being disposed on an end of the anchor bar, the engagement end being configured to an engage the catch at a location spaced apart from the interior surface of the dilator lumen irrespective of a rotational orientation of the anchor bar relative to the shoulder.

7. A system for placement of a feeding tube apparatus into the stomach of a patient using an elongate pull wire having an anchor structure attached to an end thereof, the system comprising:
   an elongate pull wire having an anchor structure fixedly connected to an end thereof, the anchor structure comprising an engagement end movable between a collapsed position adjacent to the pull wire and an expanded position spaced apart from the pull wire; and
   a feeding tube apparatus comprising:
      an elongate tubular portion having a feeding lumen extending through at least a portion thereof and configured to traverse a stoma through the patient's stomach and abdominal walls;
      a bolster fixedly connected to a proximal end of the tubular portion, the bolster having an enlarged cross-section configured to prevent egress thereof through the stoma; and
      a tapered dilator connected to a distal end of the tubular portion and having a distal tip at the distal end thereof, the dilator comprising a dilator lumen extending proximally from the distal tip, the dilator further comprising a coupling structure disposed within the dilator lumen and proximal of the distal tip, the coupling structure including a catch circumferentially disposed about an interior surface of the dilator lumen, the catch being configured to engage the engagement end of the anchor structure when in the expanded position,
   the system further comprising a tubular insert disposed within the dilator lumen, the insert comprising a proximal end that forms the catch, wherein the insert comprises a metal material having a rigidity that is greater than a rigidity of the dilator.

8. The system according to claim 7 wherein the dilator comprises a wall having an interior surface, and the insert is disposed in a recess formed in the interior surface of the wall.

9. The system according to claim 7, wherein the insert comprises a lumen extending proximally from a distal end of the insert, the distal end of the lumen having a diameter that is equal to a diameter of an adjacent portion of the dilator lumen.

10. The system according to claim 9 wherein a proximal end of the lumen of the insert has a diameter that is less than the diameter of the distal end of the lumen.

11. The system according to claim 9 wherein the lumen of the insert is adapted for the passage of the pull wire and anchor structure there through.

12. The system according to claim 1 wherein the feeding tube apparatus comprises a percutaneous endoscopic gastrostomy feeding tube adapted for delivery of nutritional products directly into a patient's stomach, the tubular portion of the feeding tube apparatus being adapted to extend percutaneously through the patient's abdominal and stomach walls, wherein the bolster comprises an internal bolster adapted to engage an interior wall of the patient's stomach, the feeding tube apparatus further comprising an external bolster attached to the tubular portion distally of the internal bolster and adapted to engage an exterior wall of the patient's abdomen.

13. The system according to claim 12 wherein the dilator is configured to facilitate ingress of the feeding tube apparatus into the patient's gastrointestinal tract and out through the patient's abdominal and stomach walls, the dilator being adapted to be removable after the tubular portion of the feeding tube apparatus is extended percutaneously through the patient's abdominal and stomach walls.

14. A method of connecting an elongate pull wire to a feeding tube apparatus comprising the steps of:
   a) providing an elongate pull wire having an anchor structure fixedly connected to an end thereof, the anchor structure comprising an engagement end movable between a collapsed position adjacent to the pull wire and an expanded position spaced apart from the pull wire;
   b) providing a feeding tube apparatus comprising an elongate tubular portion having a feeding lumen extending through at least a portion thereof, a bolster fixedly connected to a proximal end of the tubular portion, and a tapered dilator connected to a distal end of the tubular portion, the dilator comprising a dilator lumen extending proximally from a distal end of the dilator, a coupling structure disposed within the dilator lumen and proximal of the distal end, the coupling structure including a catch circumferentially disposed about an interior surface of the dilator lumen and configured to engage the engagement end of the anchor structure when in the expanded position, the catch comprising a shoulder extending completely about the interior surface of the dilator, the shoulder comprising a uniform profile configured to engage the engagement end of the anchor structure irrespective of a rotational orientation of the anchor structure relative thereto;

c) collapsing the anchor structure into the collapsed position and inserting the anchor structure into the distal end of the dilator lumen;

d) advancing the anchor structure and pull wire proximally through the dilator lumen until the anchor structure is disposed proximally of the catch of the coupling structure;

e) expanding the anchor structure into the expanded position; and f) pulling the pull wire in a distal direction so as to engage the catch of the coupling structure with the engagement end of the anchor structure.

15. The method of claim 14 further comprising the step of:

g) pulling the pull wire in the distal direction so as to pull feeding tube apparatus into and through a stomach of a patient, and subsequently through an abdominal wall of the patient.

16. A system for placement of a feeding tube apparatus into the stomach of a patient using an elongate pull wire having an anchor structure attached to an end thereof, the system comprising:

an elongate pull wire having an anchor structure fixedly connected to an end thereof, the anchor structure comprising an engagement end movable between a collapsed position adjacent to the pull wire and an expanded position spaced apart from the pull wire; and a feeding tube apparatus comprising:

an elongate tubular portion having a feeding lumen extending through at least a portion thereof and configured to traverse a stoma through the patient's stomach and abdominal walls;

a bolster fixedly connected to a proximal end of the tubular portion, the bolster having an enlarged cross-section configured to prevent egress thereof through the stoma; and a tapered dilator connected to a distal end of the tubular portion and having a distal tip at the distal end thereof, the dilator comprising a dilator lumen extending proximally from the distal tip, the dilator further comprising a coupling structure disposed within the dilator lumen and proximal of the distal tip, the coupling structure including a catch configured to engage the engagement end of the anchor structure when in the expanded position, wherein a tubular insert is disposed within the dilator lumen, the insert comprising a proximal end that forms the catch, wherein the insert comprises a metal material having a rigidity that is greater than a rigidity of the dilator, and wherein the insert comprises a lumen extending proximally from a distal end of the insert, the distal end of the lumen having a diameter that is equal to a diameter of an adjacent portion of the dilator lumen.

17. The system according to claim 16 wherein a proximal end of the lumen of the insert has a diameter that is less than the diameter of the distal end of the lumen.

18. The system according to claim 16 wherein the lumen of the insert is adapted for the passage of the pull wire and anchor structure there through.

* * * * *